United States Patent [19]

Fukui et al.

[11] Patent Number: 5,087,568
[45] Date of Patent: Feb. 11, 1992

[54] PROCESS FOR PREPARATION OF SUPEROXIDE DISMUTASE

[75] Inventors: Kiyoshi Fukui; Fumio Kubo, both of Ube; Masayuki Watanabe, Ogori, all of Japan

[73] Assignee: UBE Industries, Ltd., Yamaguchi, Japan

[21] Appl. No.: 155,157

[22] Filed: Feb. 11, 1988

[30] Foreign Application Priority Data

Feb. 14, 1987 [JP] Japan .................................. 62-31928

[51] Int. Cl.$^5$ ............................................. C12N 9/02
[52] U.S. Cl. ................................................ 435/189
[58] Field of Search ................ 435/172.3, 189; 935/14

[56] References Cited

U.S. PATENT DOCUMENTS 4,742,004  5/1988  Hartman et al. ............... 435/172.3 X

OTHER PUBLICATIONS

Developments in Biochemistry, 11A, 223 (1980) pp. 223-229.
Biochem. Biophys. Acta, 537, 86 (1978), pp. 86-99.
Patel, In *Biotechnology, Applications and Research*, eds. Cheremisnoff and Ouellette. Technomic Publishers, Lancaster, PA., 1985, pp. 553-554.

Primary Examiner—Richard A. Schwartz
Assistant Examiner—S. L. Nolan
Attorney, Agent, or Firm—Wenderoth, Lind & Ponack

[57] ABSTRACT

A process for producing recombinant human Cu, Zn-superoxide dismutase, which comprises treating a solution of copper-free or copper-deficient recombinant human Cu, Zn-superoxide dismutase with a copper salt in the presence of $\beta$-mercaptoethanol.

3 Claims, 2 Drawing Sheets

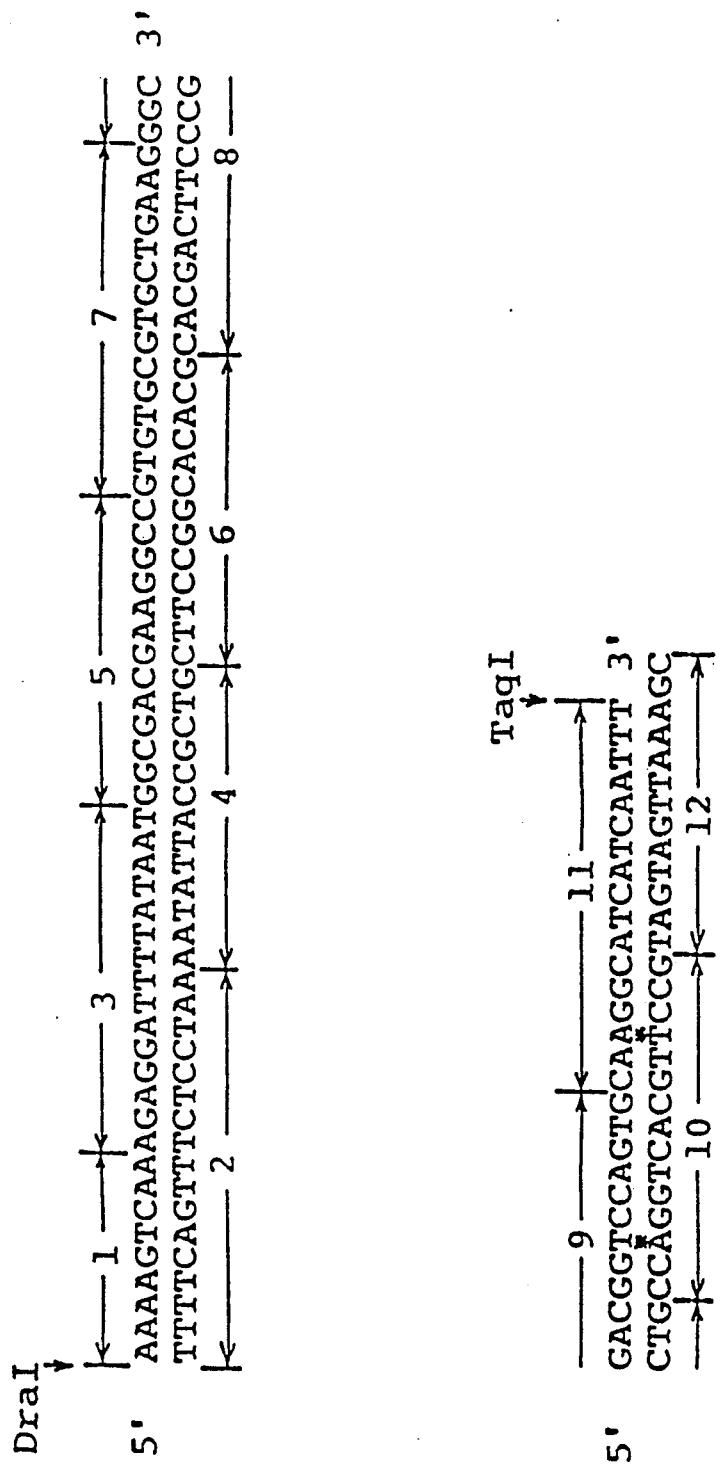

PROCESS FOR PREPARATION OF SUPEROXIDE DISMUTASE

BACKGROUND OF THE INVENTION

This invention relates to a process for producing recombinant human Cu,Zn-superoxide dismutase (to be referred to as "recombinant human SOD"). More specifically, it relates to a process for producing recombinant human SOD which comprises treating an apoenzyme of recombinant human superoxide dismutase with a copper salt in the presence of $\beta$-mercaptoethanol.

Human SOD is a metalloenzyme having the action of scavenging superoxide ($.O_2^-$) in accordance with a disproportionation reaction of the following formula.

$$2.O_2^- + 2H^+ \xrightarrow{\text{human SOD}} O_2 + H_2O_2$$

Hence, human SOD is expected to be an effective therapeutic agent for tissue damage induced by superoxide generated from oxygen in vivo, for example inflammation, arthrosis deformans, chronic articular rheumatism, radiation damage, ultraviolet damage, retrolentri fibroplasia, cataract, side-effects of anticancer agents such as adriamycin, and injuries associated with reperfusion of blood to an ischemic part.

Methods have already been disclosed for the production of human SOD from human cells or tissues (see Japanese Laid-Open Patent Publications Nos. 141288/1982, 155991/1982 and 91881/1984). These methods, however, are not entirely suitable for industrial production because the raw materials are difficult to obtain in large quantities, and human placenta as a relatively easily available material has a low SOD content.

Much work has been done on the production of human SOD by the gene recombinant technology, and various methods have been disclosed to date (see Japanese Laid-Open Patent Publications Nos. 137286/1985, 111690/1986, 111693/1986 and 139390/1986). As stated in Japanese Laid-Open Patent Publication No. 111693/1986, recombinant human SOD accumulated as an intracellular product obtained by cultivating a microorganism transformed with a recombinant DNA having a human SOD structural gene downstream of an expression regulatory gene has quite the same amino acid sequence as natural human SOD. However, it does not contain a theoretical amount of a copper ion which is the active site of human SOD, and therefore has low enzyme activity.

J. C. Dinbar, B. Holmquist and J. T. Johansen reported (Biochemistry, 23, 4330–4335, 1984) that when a Cu-free apoenzyme of Cu,Zn-SOD is treated with a copper salt, a copper ion is taken into the apoenzyme to recover enzyme activity.

We therefore extensively studied the method of treating an apoenzyme of recombinant human SOD in a solution of a copper salt in order to produce recombinant human SOD containing a theoretical amount of a copper ion and having high enzyme activity. Consequently, we have succeeded in obtaining recombinant human SOD containing a theoretical amount of a copper ion and having high enzyme activity. However, this method gives rise to a new problem in that it gives recombinant human SODs having different electric charges and different molecular weights as shown by their electrophoresis.

SUMMARY OF THE INVENTION

It is an object of this invention therefore to provide a novel process for producing human SOD containing a theoretical amount of a copper ion and having high enzyme activity.

Another object of this invention is to provide a novel process for producing recombinant human SOD which contains a theoretical amount of a copper ion and has high enzyme activity, a uniform electric charge and a uniform molecular weight.

Still another object of this invention is to provide a novel process which comprises treating an apoenzyme of recombinant human SOD with a copper salt in the presence of $\beta$-mercaptoethanol.

Other objects of the invention along with its advantages will become apparent from the following description.

According to this invention, these objects and advantages of the invention are achieved by a process for producing recombinant human Cu,Zn-SOD, which comprises treating a solution of copper-free or copper-deficient recombinant human SOD with a copper salt in the presence of $\beta$-mercaptoethanol.

BRIEF DESCRIPTION OF THE DRAWINGS

FIG. 2 shows division of 84 bp synthetic DNA into 12 nucleotides.

DETAILED DESCRIPTION OF THE INVENTION

Figure 1:
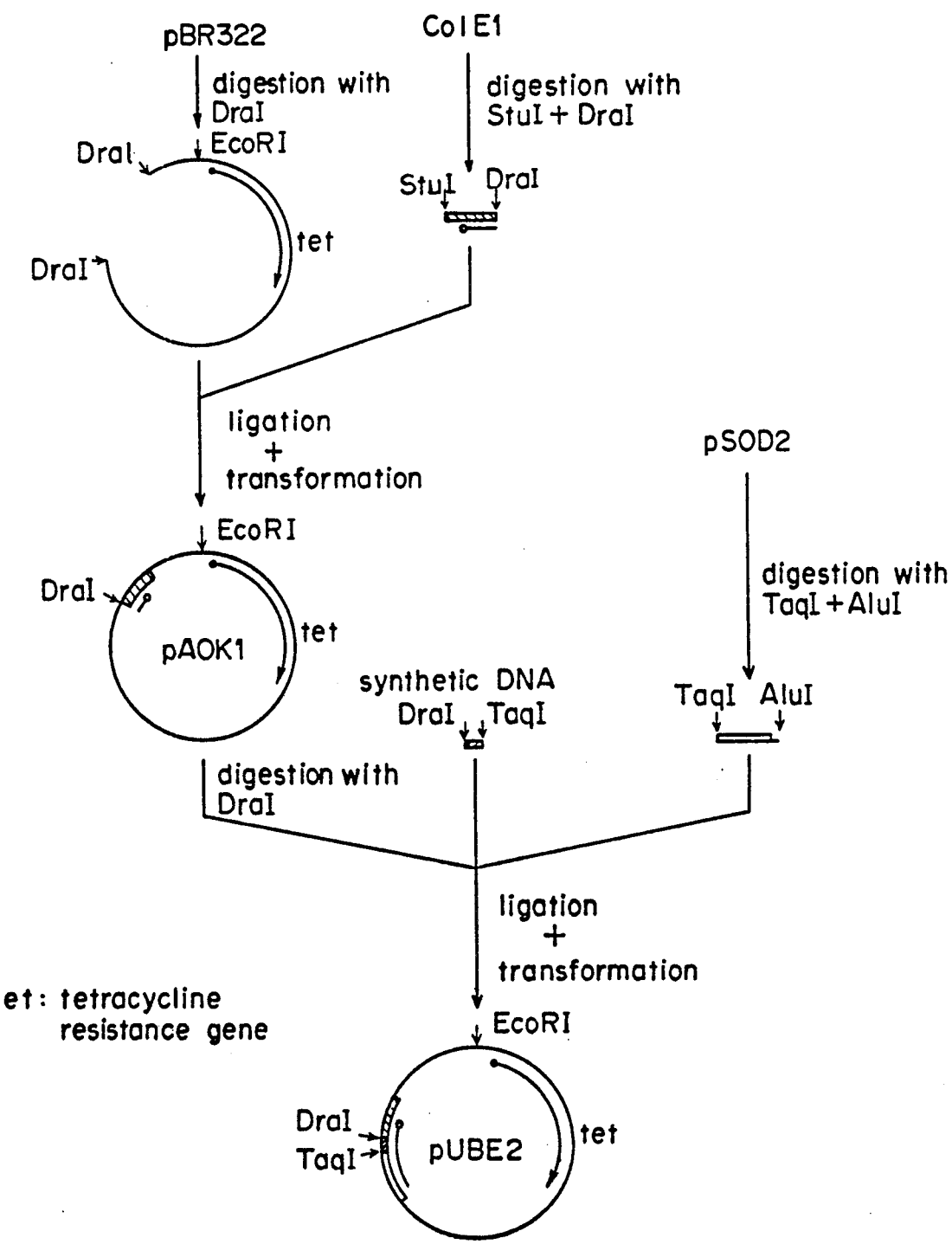
FIG. 1 shows a strategy for constructing a plasmid for expression of recombinant human SOD.

The Cu-free or Cu-deficient recombinant human SOD, which is used in this invention, can be produced by cultivating a microorganism transformed with a recombinant DNA having a human SOD structural gene downstream of an expression regulatory gene. Accordingly, the solution of the apoenzyme can be prepared, for example by the following procedure, from the culture broth obtained by the cultivation.

Solution A

A microorganism transformed with a recombinant DNA having a human SOD structural gene downstream of an expression regulatory gene is cultivated to allow the microorganism to produce recombinant human SOD. Then, the microorganism cells are harvested from the culture broth in a customary manner such as centrifugation. The cells are suspended in a suitable aqueous solution (5 to 50 ml per gram of the wet cells) having a pH of 5.0 to 8.0, and the cells are disrupted by known methods. The lysate is centrifuged to obtain a supernatant.

Solution B

Ammonium sulfate is added to the solution A so that its concentration is 50% to 70% of the saturation at 0° C. The mixture is stirred at 0° to 25° C. for 3 hours to 1 day, and then centrifuged to obtain a supernatant.

The starting material used in the process of this invention, however, is not limited to the above solutions A and B. Solutions obtained by further treating these solutions for purification of recombinant human SOD may also be used in the process of this invention.

The copper salt used in the process of this invention preferably includes divalent copper salts having a negative ion of organic or inorganic acids. Specific examples are cupric chloride, cupric nitrate, cupric sulfate and cupric acetate.

The amount of the copper salt used is, for example, $0.15 \times 10^{-6}$ to $15 \times 10^{-6}$ mole per gram of the wet cells. Treatment with the copper salt is carried out, for example, by adding an aqueous solution of the copper salt to the solution containing Cu-free or Cu-deficient recombinant human SOD at 0° C. to room temperature, and allowing the mixture to stand, or stirring it, at 0° C. to room temperature, preferably below about 4° C., for 10 minutes to 1 day.

The preferred concentration of $\beta$-mercaptoethanol in the solution to be treated ranges from 5 to 100 mM. The desired recombinant human SOD containing a theoretical amount of copper and having high enzyme activity, a uniform electric charge and a uniform molecular weight can be obtained by isolating a protein having SOD activity by known protein purification methods after the treatment with the copper salt in the presence of $\beta$-mercaptoethanol. The purification may be carried out, for example, by heat-treatment, salting out, concentration, dialysis, ion-exchange chromatography, gel filtration chromatography, chromatofocusing, electrophoresis, high-performance liquid chromatography and affinity chromatography in suitable combinations.

The following Examples and Referential Examples will illustrate the present invention without any intention of limiting its scope thereby.

REFERENTIAL EXAMPLE 1

Construction of plasmid pSOD2 having human SOD cDNA:

RNA was isolated by the guanidium-cesium chloride method from human placenta obtained by normal parturition, and then mRNA having a poly(A) tail was separated by using oligo(dT) cellulose.

A cDNA library was constructed from the resulting mRNA in accordance with the Okayama-Berg method using E. coli DH1 as a host organism.

By the colony hybridization method, E. coli DH1 (pSOD2) harboring plasmid pSOD2 having human SOD cDNA was obtained. The plasmid pSOD2 was isolated from this microorganism strain by a customary method.

REFERENTIAL EXAMPLE 2

Construction of recombinant DNA for expression of human SOD:

A plasmid for expression of recombinant human SOD was constructed in accordance with the strategy shown in FIG. 1 by linking human SOD structural gene to the downstream end of the expression regulatory gene of colicin E1 gene. (1) Construction of plasmid pAOK1 having an expression regulatory gene fragment of colicin E1 gene:

Colicin E1 DNA was digested with DraI and subsequently with StuI. The digestion product was subjected to 5% polyacrylamide gel electrophoresis, and a 340 bp StuI-DraI fragment was recovered by the electrophoretic elution method. The fragment was inserted into the DraI site of plasmid pBR322 to prepare plasmid pAOK1.

(2) Preparation of a human SOD structural gene fragment:

Plasmid pSOD2 was digested with AluI and subsequently with TagI. The digestion product was subjected to 5% polyacrylamide gel electrophoresis, and a 440 bp TagI-AluI fragment was recovered by the electrophoretic elution method.

(3) Preparation of synthetic DNA

The required portion having a size of 84 bp which was deleted in the 340 bp Col E1 fragment and SOD structural gene fragment was divided into 12 oligonucleotides as shown in FIG. 2.

(4) Construction of recombinant DNA for expression of human SOD:

The 84 bp synthetic DNA and the 440 bp SOD structural gene fragment were inserted into the DraI site of plasmid pAOK1 to obtain human SOD-expressing recombinant DNA, pUBE2, in which the human SOD structural gene was linked to the downstream end of the expression regulatory gene of the colicin E1 gene.

REFERENTIAL EXAMPLE 3

Preparation of human SOD-expressing recombinant E. coli W3110 (pUBE2) (Deposit No. 634 at Fermentation Research Institute, Japan):

E. coli W3110 cultivated in SOB medium to an $OD_{550}$ of 0.55 was treated first with TfbI and then with TfbII, and plasmid pUBE2 was added to the treated solution. The mixture was left to stand at 0° C. for 30 minutes and then at 42° C. for 90 seconds to obtain E. coli W3110 (pUBE2) harboring plasmid pUBE2.

REFERENTIAL EXAMPLE 4

Cultivation of recombinant E. coli W3110 (pUBE2) and induction of synthesis of recombinant human SOD:

E. coli W3110 (pUBE2) was inoculated in 100 liters of a sterilized medium containing 300 g of Casamino acid, 400 g of glucose, 1 g of tetracycline, 600 g of $Na_2HPO_4$, 300 g of $KH_2PO_4$, 50 g of NaCl, 100 g of $NH_4Cl$, 24 g of $MgSO_4$, 1.11 g of $CaCl_2$, 540 mg of $CuCl_2.2H_2O$, 880 mg of $ZnSO_4.7H_2O$, 600 mg of $FeSO_4.7H_2O$, 150 mg of $MnSO_4.H_2O$, 150 mg of $AlCl_3.6H_2O$ and 7.5 mg of $H_3BO_3$, and cultivated at 37° C. and a pH of 7.1 to 7.4 while the medium was stirred and aerated so as to maintain the concentration of dissolved oxygen at 2 ppm or more.

After performing the cultivation to an $OD_{550}$ of 0.4, 2 liters of an aqueous solution containing 600 g of $Na_2PO_4$, 300 g of $KH_2PO_4$, 50 g of NaCl and 100 g of $NH_4Cl$, 1 liter of an aqueous solution containing 100 g of glucose, and 0.5 liter of an aqueous solution containing 200 mg of mitomycin C were sequentially added to induce synthesis of recombinant human SOD at 37° C. for 2 hours.

The cultivation mixture was then centrifuged to obtain 325 g of wet cells.

REFERENTIAL EXAMPLE 5

Two hundred grams of the wet cells obtained in Referential Example 4 were suspended in 500 ml of 10 mM triethanolamine buffer (pH 7.0) and disrupted by a French press. The lysate was centrifuged at 10800 G for 60 minutes, and then 10 mM triethanolamine buffer (pH 7.0) was added to the resulting supernatant to adjust the total amount to 2 liters. The solution was heat-treated for 5 minutes at 60° C., and the resulting precipitate was removed by centrifugation at 10800 G for 30 minutes. Ammonium sulfate (828.4 g) was added to the supernatant, and the mixture was stirred overnight at about 4° C. The precipitate was removed by centrifugation (13700 G, 15 minutes). Ammonium sulfate (501.6 g) was added to the supernatant, and the mixture was stirred for 3 hours at about 4° C. The precipitate was collected by centrifugation (13700 G, 15 minutes). The precipitate was dissolved in 10 mM triethanolamine buffer (pH 7.0), and the solution was dialyzed three times against 2.5 liters of 10 mM triethanolamine buffer (pH 7.0). The solution obtained by dialysis was passed through a column of Q-Sepharose FF (made by Pharmacia Co.) equilibrated with 10 mM triethanolamine buffer (pH 7.0). The column was washed with 1 liter of 10 mM triethanolamine buffer (pH 7.0), and eluted with 30 mM NaCl-10 mM trielhanolamine buffer (pH 7.0). 460 ml of human SOD-containing fractions were collected. To the 230 ml of the human SOD-containing solution 160 g of ammonium sulfate was added. The mixture was stirred for 6 hours at about 4° C. The resulting precipitate was collected by centrifugation (10800 G, 30 minutes), dissolved in water, and dialyzed three times against 2.5 liters of water. The dialyzate was filtered through a 0.2-μm filter and lyophilized to obtain 878 mg of a colorless solid. The amounts of copper and zinc in this sample were analyzed by a plasma excited emission spectrophotometer, and the specific activity was measured by the McCord-Fridovich method [J. Biol. Chem., 244, 6049 (1969)].

Amount of copper: 0.21 gram-atom/molecule
Amount of zinc: 2.40 gram-atom/molecule
Specific activity: 850 U/mg

REFERENTIAL EXAMPLE 6

To the remainder (230 ml) of the SOD-containing solution obtained in Referential Example 5 were added 8.8 g of NaCl, 15 ml of 2 M aqueous solution of acetic acid, 0.15 ml of 1 M aqueous solution of $CuCl_2$ and water to prepare 300 ml of a solution. The pH of the solution was adjusted to 5.0 with an aqueous solution of NaOH. The mixture was stirred overnight at about 4° C., and its pH was adjusted to 7.0 with an aqueous solution of NaOH. Ammonium sulfate (278.8 g) was added to the solution, and the mixture was stirred for 2 hours at about 4° C. The resulting precipitate was collected by centrifugation, dissolved in water, and dialyzed three times against 2.5 liters of water. The dialyzate was filtered through a 0.2-μm filter, and lyophilized to give 818 mg of a pale blue solid. The amounts of copper and zinc and the specific activity were measured, and the results were as follows.

Amount of copper: 1.56 gram-atom/molecule
Amount of zinc: 1.21 gram-atom/molecule
Specific activity: 3520 U/mg

REFERENTIAL EXAMPLE 7

One hundred grams of the wet cells obtained in Referential Example 4 were suspended in 400 ml of 10 mM triethanolamine buffer (pH 7.0), and disrupted by a French press. The lysate was centrifuged (10800 G, 60 minutes). To the resulting supernatant was added 10 mM triethanolamine buffer (pH 7.0) to prepare 1 liter of a solution. Then, 0.2 ml of a 0.5 M aqueous solution of $CuSO_4$ was added to the resulting solution, and the mixture was stirred overnight at about 4° C. and then heat-treated at 60° C. for 5 minutes. The resulting precipitate was removed by centrifugation (10800 G, 30 minutes). Ammonium sulfate (410 g) was added to the supernatant, and the mixture was stirred overnight at about 4° C. The resulting precipitate was removed by centrifugation (13700 G, 15 minutes), and 248 g of ammonium sulfate was added to the resulting supernatant. The mixture was stirred for 3 hours at about 4° C., and the resulting precipitate was collected by centrifugation (13700 G, 15 minutes). The precipitate was dissolved in 10 mM triethanolamine buffer (pH 7.0), and the solution was dialyzed three times against 3 liters of 10 mM triethanolamine buffer (pH 7.0). The dialyzate was passed through a column of Q Sepharose FF (made by Pharmacia Co.) equilibrated with 10 mM triethanolamine buffer (pH 7.0). The column was washed with 1 liter of 10 mM triethanolamine buffer (pH 7.0) and then eluted with 30mM NaCl-10 mM triethanolamine buffer (pH 7.0) Human SOD-containing fractions were collected as a solution, and 216 ml of 0.5M acetate buffer (pH 5.0) and 1.1 ml of a 1 M aqueous solution of $CuCl_2$ were added to the solution. The mixture was stirred overnight at about 4° C., and its pH was adjusted to 7.0 with a 4N aqueous solution of NaOH. The mixture was centrifuged at 13700 G for 20 minutes NaCl (31.6 g) was added to the resulting supernatant, and the solution was passed through a column of Cu-supported chelating Sepharose 6B (made by Pharmacia Co.) equilibrated with 0.5M NaCl-10 mM triethanolamine buffer (pH 7.0). The column was washed with 140 ml of 0.5M NaCl-10 mM triethanolamine buffer (pH 7.0) and then with 450 ml of 0.5 M NaCl-50 mM phosphate buffer (pH 6.0), and then eluted with 50 mM glycine-0.5 M NaCl-10 mM triethanolamine buffer (pH 7.0). Human SOD-containing fractions were collected as a solution. Ammonium sulfate (439 g) was added to the solution, and the mixture was stirred for 7 hours at about 4° C. The resulting precipitate was collected by centrifugation (13700 G, 20 minutes). The collected precipitate was dissolved in 10 mM triethanolamine buffer (pH 7.0) and dialyzed against 10 mM triethanolamine (pH 7.0). The dialyzate was passed through a column of MonoQ (made by Pharmacia Co.) equilibrated with 10 mM triethanolamine buffer (pH 7.0), and eluted with NaCl-10 mM triethanolamine buffer to obtain three SOD-containing fractions. These fractions were eluted at a NaCl concentration of 60 mM (fraction A), 80 mM (fraction B) and 90 mM (fraction C), respectively. The fractions were salted out with ammonium sulfate to recover proteins. They were dialyzed against water and lyophilized. The amounts yielded, the metal contents and the specific activity of these SODs and their molecular weights determined by SDS-PAGE are shown below.

Fraction A

Amount yielded: 182 mg
Amount of copper: 1.92 gram-atom/molecule
Amount of zinc: 2.01 gram-atom/molecule
specific activity: 4906 U/mg
Molecular weight: 16.4 K, 17 K Fraction B Amount yielded: 357 mg
Amount of copper: 1.87 gram-atom/molecule
Amount of zinc: 2.09 gram-atom/molecule
Specific activity: 4770 U/mg
Molecular weight: 16.4 K, 17 K, 18 K Fraction C Amount yielded: 17 mg
Amount of copper: 1.78 gram-atom/molecule
Amount of zinc: 1.93 gram-atom/molecule
Specific activity: 3752 U/mg
Molecular weight: 17 K, 18 K

REFERENTIAL EXAMPLE 8

One hundred grams of the wet cells obtained by the same method as in Referential Example 4 were suspended in 400 ml of water, and disrupted by a French press. The lysate was centrifuged (13700 G, 60 minutes), and water was added to the resulting supernatant to 600 ml. Sodium acetate (8.2 g) and 35 g of NaCl were added to the solution and its pH was adjusted to 5.0 with 6N HCl. Water was added to adjust the total amount to 1 liter. To the mixture was added 0.5 ml of a 1 M aqueous solution of CuCl2 The mixture was stirred for 1 day at about 4° C., and 10 ml of 1 M trielhanolamine buffer (pH 7.0) was added. The pH of the mixture was adjusted to 7.0 with a 4N aqueous solution of NaOH. The mixture was stirred overnight at about 4° C., and then centrifuged at 13700 G for 30 minutes. To the resulting supernatant was added 416 g of ammonium sulfate, and the mixture was stirred for 7 hours at about 4°) C. The resulting precipitate was removed by centrifugation at 13700 G for 30 minutes. Ammonium sulfate (234 g) was added to the supernatant, and the mixture was stirred overnight at about 4° C. The precipitate was collected by centrifugation at 13700 G for 30 minutes. The precipitate was dissolved in water, and dialyzed three times against 3 liters of 2 mM phosphate buffer (pH 7.0) and further three times against 10 mM triethanolamine buffer (pH 7.0). The dialyzates were passed through a column of Q-Sepharose FF (made by Pharmacia Co.) equilibrated with 10 mM triethanolamine buffer (pH 7.0). The column was washed with 1 liter of 10 mM triethanolamine buffer (pH 7.0) and eluted with 30 mM NaCl-10 mM triethanolamine buffer (pH 7.0). Human SOD-containing fractions were collected as a solution. NaCl (12.5 g) was added to the solution, and the mixture was passed through a column of copper-supported chelating Sepharose 6B (made by Pharmacia Co.) equilibrated with 0.5M NaCl-10 mM triethanolamine buffer (pH 7.0). The column was washed with 300 ml of 0.5M NaCl-10 mM triethanolamine buffer (pH 7.0) and then with 1500 ml of 0.5M NaCl-50 mM phosphate buffer (pH 6.0) and then eluted with 50 mM glycine-O.5M NaCl-10 mM triethanolamine buffer (pH 7.0). Human SOD-containing fractions were collected as a solution. Ammonium sulfate (378 g) was added to the solution, and the mixture was stirred for 7 hours at about 4° C. The resulting precipitate was collected by centrifugation at 13700 G for 20 minutes, dissolved in 10 mM triethanolamine buffer (pH 7.0), and dialyzed against 10 mM triethanolamine buffer (pH 7.0). The dialyzate was passed through a column of MonoQ (made by Pharmacia Co.) equilibrated with 10 mM triethanolamine buffer (pH 7.0), and eluted with NaCl-10 mM triethanolamine buffer (pH 7.0) to obtain three fractions as in Referential Example 7. The amounts yielded, metal contents, specific activity and molecular weights by SDS-PAGE of the SODs were measured, and are shown below.

Fraction A

Amount yielded: 142 mg
Amount of copper: 1.93 gram-atom/molecule
Amount of zinc: 1.99 gram-atom/molecule
Specific activity: 5300 U/mg
Molecular weight: 17 K

Fraction B

Amount yielded: 200 mg
Amount of copper: 1.85 gram-atom/molecule
Amount of zinc: 1.90 gram-atom/molecule
Specific activity: 4800 U/mg
Molecular weight: 17 K, 18 K

Fraction C

Amount yielded: 32 mg
Amount of copper: 1.84 gram-atom/molecule
Amount of zinc: 1.93 gram-atom/molecule
Specific activity: 4500 U/mg
Molecular weight: 17 K, 18 K

EXAMPLE 1

Wet cells (150 g) obtained by the same way as in Referential Example 4 were suspended in 600 ml of water, and disrupted by a French press. The lysate was centrifuged at 10800 G for 60 minutes. To the resulting supernatant were added 300 ml of 0.5M acetate buffer (pH 5.0) and 43.8 g of NaCl, and then water was added to 1.5 liters. Then, 0.75 ml of a 1 M aqueous solution of CuCl$_2$ was added to the solution, and the mixture was stirred for 1 day at about oC Then, 1.7 g of β-mercaptoethanol was added. The mixture was adjusted to pH 7.0 with an aqueous solution of NaOH, and stirred overnight at about 4° C. Ammonium sulfate (680 g) was added to the mixture, and the mixture was stirred for 3 hours at about 4° C. and centrifuged (10800 G, 15 minutes). Ammonium sulfate (387 g) was added to the supernatant, and the mixture was stirred overnight at about 4° C. The resulting precipitate was collected by centrifugation (10800 G, 15 minutes), dissolved in 10 mM triethanolamine buffer (pH 7.0), and dialyzed against 10 mM triethanolamine buffer (pH 7.0). The dialyzate was passed through a column of DEAE Sepharose FF (made by Pharmacia Co.) equilibrated with 10 mM triethanolamine buffer (pH 7.0). The column was washed with 1 liter of 10 mM triehanolamine buffer (pH 7.0) and then eluted with 30 mM NaCl-10 mM triethanolamine buffer (pH 7.0). Human SOD-containing fractions were collected as a solution. Sodium acetate trihydrate (47.6 g) and 102.3 g of NaCl were added to the solution, and the pH of the mixture was adjusted to 5.0 with HCl. Then, 90 μl of a 1 M aqueous solution of CuCl$_2$ was added. The mixture was stirred overnight at about 4° C. The pH of the solution was adjusted to 7.0 with an aqueous solution of NaOH, and the solution was passed through a column of copper-supported chelating Sepharose 6B (made by Pharmacia Co.) equilibrated with 0.5M NaCl-10 mM triethanolamine buffer (pH 7.0). The column was washed with 350 ml of 0.5M NaCl-10 mM triethanolamine buffer (pH 7.0) and then with 1800 ml of 0.5M NaCl-50 mM phosphate buffer (pH 6.0), and then eluted with 50 mM glycine-0.5M NaCl-10 mM triethanolamine buffer (pH 7.0). Human SOD-containing fractions were collected as a solution. Ammonium sulfate (355.5 g) was added to the solution, and the mixture was stirred for 4 hours at about 4° C. The resulting precipitate was collected by centrifugation (13700 G, 20 minutes), and dialyzed against 10 mM triethanolamine buffer (pH 7.0). The dialyzate was passed through a column of Q-Sepharose FF (made by Pharmacia Co.) equilibrated with 10 mM triethanolamine buffer (pH 7.0). The column was washed with 500 ml of 10 mM triethanolamine buffer (pH 7.0) and eluted with 20 mM NaCl-10 mM triethanolamine buffer (pH 7.0). Human SOD-containing fractions were collected as a solution. Amonium sulfate (781 g) was added to the solution, and the mixture was stirred for 4 hours at about 4° C. The precipitate was solved in water, and dialyzed against water. The dialyzate was lyophilized to give a pale bluish green solid. The amount yielded, metal contents, specific activity and molecular weight in SDS electrophoresis of the product are shown below.

Amount yielded: 933 mg
Amount of copper: 2.02 gram-atom/molecule
Amount of zinc: 1.99 gram-atom/molecule
Specific activity: 5320 U/mg
Molecular weight: 17 K

EXAMPLE 2

One hundred grams of wet cells obtained in the same way as in Referential Example 4 were suspended in 10 mM triethanolamine buffer (pH 8.0), and disrupted by a French press. To the lysate was added 10 mM triethanolamine buffer (pH 8.0) to 800 ml. The suspension was centrifuged at 13700 G for 60 minutes. To the supernatant was added 10 mM triethanolamine buffer (pH 8.0) to adjust the total amount to 1 liter. Ammonium sulfate (436 g) was added, and the mixture was stirred at about 4° C. for 3 hours. The resulting precipitate was removed by centrifugation (13700 G, 20 minutes). To the supernatant were added 0.78 g of $\beta$-mercaptoethanol and 0.5 ml of a 1 M aqueous solution of $CuCl_2$. The mixture was stirred overnight at about 4° C. Ammonium sulfate (240 g) was added to the mixture, and the mixture was further stirred at about 4° C. for 3 hours. The precipitate was collected by centrifugation (13700 G, 15 minutes) and worked up in the same way as in Example 1 to give recombinant human SOD. The amount yielded, metal contents, specific activity and molecular weight by SDS electrophoresis of the product were as shown below.

Amount yielded: 506 mg
Amount of copper: 2.00 gram-atom/molecule
Amount of zinc: 1.96 gram-atom/molecule
Specific activity: 5040 U/mg
Molecular weight: 17 K

What we claim is:

1. A process for producing recombinant human Cu, Zn-superoxide dismutase, which comprises contacting a solution of recombinant human Cu,Zn-superoxide dismutase free from copper or containing less than 2 gram atoms of copper per molecule of superoxide dismuta, with a copper salt in the presence of $\beta$-mercaptoethanol, and recovering the obtained recombinant human Cu,Zn-superoxide dismutase from the resultant reaction mixture.

2. The process of claim 1 wherein the copper salt is a cupric salt.

3. The process of claim 1 wherein the concentration of $\beta$-mercaptoethanol is 5 to 100 mM in said solution.

* * * * *